United States Patent [19]

Harding et al.

[11] Patent Number: 5,265,144
[45] Date of Patent: Nov. 23, 1993

[54] X-RAY APPARATUS

[75] Inventors: Geoffrey Harding, Hamburg; Gerhard Martens, Henstedt-Ulzburg, both of Fed. Rep. of Germany

[73] Assignee: U.S. Philips Corp., New York, N.Y.

[21] Appl. No.: 821,511

[22] Filed: Jan. 15, 1992

[30] Foreign Application Priority Data

Jan. 19, 1991 [DE] Fed. Rep. of Germany ....... 4101544

[51] Int. Cl.$^5$ ...................... G01N 23/201; G01T 1/36
[52] U.S. Cl. ...................................... 378/86; 378/147; 378/88; 378/149
[58] Field of Search ...................... 378/86, 87, 70, 147, 378/62, 88, 149; 250/363.08, 363.1

[56] References Cited

U.S. PATENT DOCUMENTS

| | | | |
|---|---|---|---|
| 4,203,037 | 5/1980 | Gur et al. | 378/62 |
| 4,597,096 | 6/1986 | Larsson | 250/363.10 |
| 4,754,469 | 6/1988 | Harding et al. | 378/88 |
| 4,792,686 | 12/1988 | Karcher et al. | 250/363.10 |
| 4,825,454 | 4/1989 | Annis et al. | 378/87 |
| 5,007,072 | 4/1991 | Jenkins et al. | 378/88 |
| 5,008,911 | 4/1991 | Harding | 378/86 |
| 5,099,134 | 3/1992 | Hase et al. | 250/363.10 |

FOREIGN PATENT DOCUMENTS 0209952 1/1987 European Pat. Off. .
0360347 3/1990 European Pat. Off. .
3712928 11/1988 Fed. Rep. of Germany .
1463054 2/1977 United Kingdom .

OTHER PUBLICATIONS

"Energy-dispersive X-ray Diffraction Tomograhy" by G. Harding et al, Phys. Med. Biol., 1990, vol. 35, No. 1, 33-41.

Primary Examiner—David P. Porta
Assistant Examiner—Kim-Kwok Chu
Attorney, Agent, or Firm—Jack D. Slobod

[57] ABSTRACT

An X-ray apparatus comprises a polychromatic X-ray source for generating a primary beam of small cross-section, an energy-sensitive detector arrangement for detecting the scattered radiation produced by elastic scattering processes in the primary beam, which detector arrangement comprises a plurality of detector elements which are arranged on rings concentric with the primary beam, and a collimator arrangement which is arranged between the X-ray source and the detector arrangement and which encloses the primary beam. In order to enable accurate determination of the pulse transfer spectrum while using a low dose, the collimator arrangement is constructed so that the scattered radiation from the same section of the primary beam is incident on a plurality of detector elements.

4 Claims, 3 Drawing Sheets

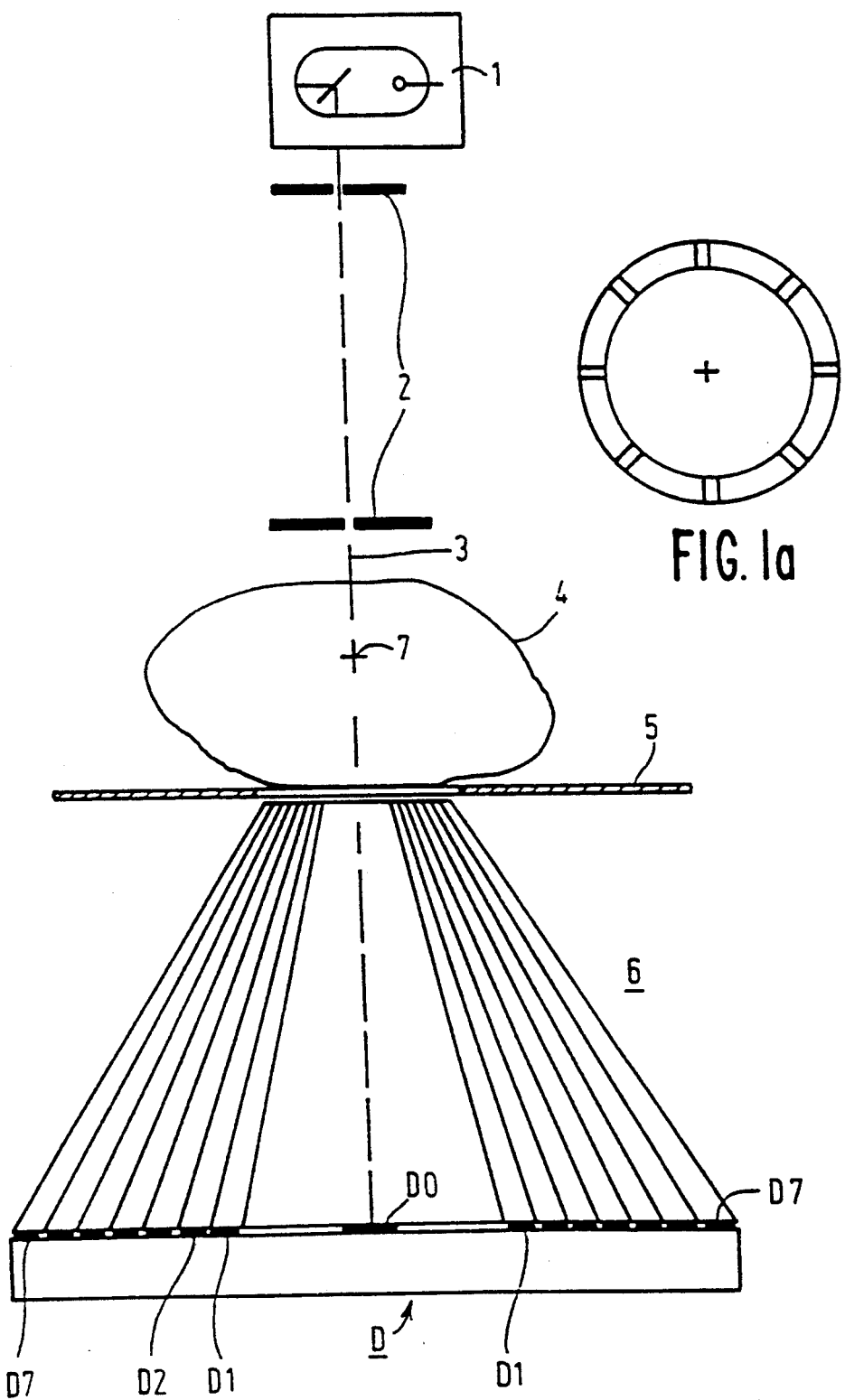
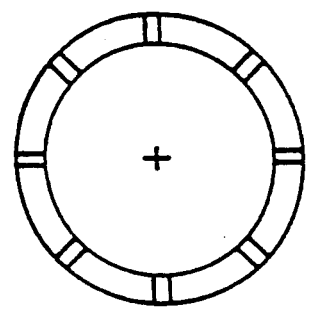
FIG. 1a
FIG. 1b

X-RAY APPARATUS

BACKGROUND OF THE INVENTION

1. Field of the Invention

The invention relates to an X-ray apparatus, comprising a polychromatic X-ray source for generating a primary beam of small cross-section, an energy-sensitive detector arrangement for detecting the scattered radiation generated by elastic scattering processes in the primary beam path, which detector arrangement comprises a plurality of detector elements which are arranged on rings concentric with the primary beam, and a collimator arrangement which is arranged between the X-ray source and the detector arrangement and which encloses the primary beam.

2. Description of the Prior Art

Of interest is commonly owned copending application Ser. No. 717,737 entitled "Arrangement for Measuring the Pulse Transmission Spectrum of X-ray Quanta" filed Jun. 19, 1991 in the name of G. Harding.

An X-ray apparatus of this kind is known essentially from DE-OS 37 12 928. Therein, the collimator arrangement is constructed so that the detector elements detect different sections of the primary beam within an examination zone and that a layer image of the scatter density can be formed when the examination zone is irradiated by the primary beam in different directions and along parallel beam paths.

It is to be noted that from GB-PS 1 463 054 an X-ray apparatus is already known which comprises an X-ray source for generating a primary beam of small cross-section and a detector arrangement for detecting the scattered radiation in the primary beam by means of a plurality of detector elements.

From the magazine "Phys. Med. Biol." (1990, Vol. 35, No., 1, pp. 33–41) there is known an X-ray apparatus whereby the pulse transfer spectrum of a small area within a human body can be determined. Because the pulse transfer spectra of healthy and diseased (affected by osteoporosis) bones are clearly distinct, a method of this kind enables evaluation of the condition of the bone issue. For the detection of the pulse transfer spectrum, the radiation scattered at a fixed scattering angle (for example, 3.5°) in the primary beam is detected by means of an energy-sensitive detector and the pulse transfer is determined in accordance with the equation $$X = \sin(T/2)/L \tag{1}$$

where T is the scatter angle and L is the wavelength of the scattered radiation. Because for elastically scattered radiation the scatter cross-sections are comparatively small, the known apparatus has a comparatively low sensitivity, so that comparatively high radiation doses are required for such examinations. The radiation dose can be reduced by increasing the fixed, predetermined angular range within which the scattered radiation is detected, but the accuracy of determination of the pulse transfer is then reduced.

SUMMARY OF THE INVENTION

It is an object of the present invention to construct an X-ray apparatus of the kind set forth so that the pulse transfer spectrum of a small volume within a large object can be comparatively accurately determined by means of a comparatively low dose.

This object is achieved in accordance with the invention in that the collimator arrangement is constructed so that the scattered radiation from the same section of the primary beam is incident on a plurality of detector elements.

Each of the detector elements detects the scattered radiation within a comparatively narrow scatter angle range so that, when the energy-sensitivity of the individual detector elements is sufficiently high, the pulse transfer spectrum can be comparatively accurately determined. Because a plurality of detector elements detect the scattered radiation from the same section and because the pulse transfer spectrum is derived from the output signals of all these detector elements, the sensitivity increase, or the radiation dose reduction, corresponds to the number of detector elements "seeing" the same section of the primary beam.

For the determination of the scatter density distribution in a layer, in a first embodiment a collimator arrangement is provided between the X-ray source and the detector arrangement, which collimator arrangement encloses the primary beam and ensures that scattered radiation from the same section of the primary beam is incident on the detector elements. In order to enable determination of the scatter density, the hardness of the primary radiation is so high (between 200 keV and 2 MeV), that the attenuation of the radiation by the photoelectric effect, the elastic (Rayleigh) scattering and pair formation are negligibly small relative to the Compton scattering. In order to enable determination of the scatter density in the various sections of the primary beam, the collimator arrangement and the detector arrangement are displaced relative to the body in the direction of the primary beam.

In another embodiment according to GB-PS 1 463 054, in which no collimator is provided between the X-ray source and the detector device, such displacement is not required. Therein, use is made of the fact that the scatter angle can be unambiguously determined from the wavelength variation resulting from the Compton scattering. The point in the primary heap) where the Compton scattering process has taken place can be determined from the scatter angle and from the position of the detector element detecting the respective scattered X-ray quantum. However, for the determination of a wavelength variation (and hence of the point in the primary beam), it is necessary to use monochromatic X-rays (in the energy range between 200 keV and 2 MeV) and an energy-sensitive detector arrangement. In contrast therewith, according to the invention, the Compton scattered radiation is not detected, but essentially the elastic (Rayleigh) scattered radiation whose wavelength does not change during scattering. The X-ray quanta in the primary beam, therefore, must have a lower energy (possibly below 200 keV). The invention requires the use of polychromatic X-rays. Energy-sensitive detector arrangement and collimator arrangement do not form alternatives in this respect, but are both required.

BRIEF DESCRIPTION OF THE DRAWING

The invention will be described in detail hereinafter with reference to the drawing.

Therein:

FIG. 1a shows a special embodiment of a detector element,

FIG. 1b shows an X-ray apparatus in accordance with an embodiment of the invention.

DESCRIPTION OF THE PREFERRED EMBODIMENT

Figure 2:
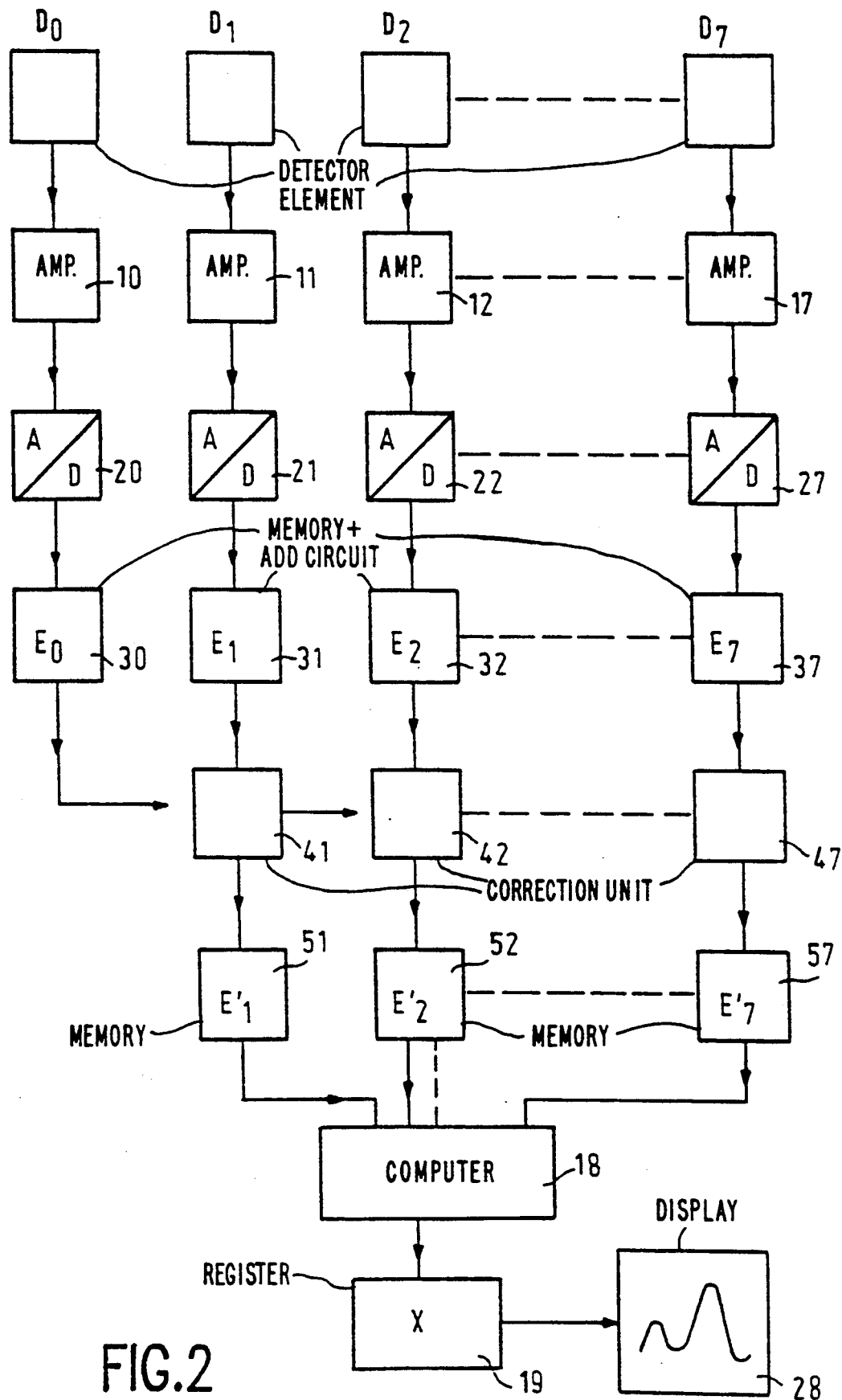
FIG. 2 shows a device for determining the pulse transfer spectrum from the output signals of the detector elements.

The reference numeral 1 in FIG. 1a denotes a polychromatic X-ray source which may comprise, for example an X-ray tube. The polychromatic X-ray source 1 emits X-rays in an energy range which, in the case of an X-ray tube, is dependent on the high voltage applied thereto. Using at least one diaphragm 2, a pencil beam 3, i.e. a primary beam of small cross-section, is formed from the X-rays generated. The primary beam passes through a large object 4, for example a patient arranged on a table top 5. Underneath the table top there is arranged a detector arrangement D which measures the intensity of the primary beam and the scattered radiation formed in the primary beam. The detector arrangement measures the X-rays in an energy-sensitive manner, i.e. its output signals (linearly) depend on the energy of the X-ray quanta detected.

The detector arrangement D comprises a circular germanium crystal which is arranged so as to be concentric with the primary beam 3 and which comprises a central detector element $D_0$ and ring-shaped detector elements $D_1 \ldots D_7$ which are arranged so as to be concentric therewith and which independently detect the X-ray quanta. The central detector element $D_0$ measures the intensity of the primary beam after its passage through the body 4, whilst the detector elements $D_1 \ldots D_7$ separately detect the scattered radiation from the examination zone. Each detector element has a width of 2 mm and a clearance of 0.5 mm exists each time between two adjacent detector elements. The outer detector element $D_7$ has an outer diameter of 70 mm.

Between the table top 5 and the detector arrangement D there is provided a collimator arrangement 6. This arrangement consists of a number of collimator laminations which are shaped as a truncated cone surface. The prolongations of the surfaces of these collimator laminations intersect in the point 7 which is marked by a cross and which is situated within the body 4. The number of collimator laminations provided at least equals the number of detector elements, the arrangement being such that the scattered radiation between neighboring collimator laminations can each time be incident on only one of the detector elements $D_1 \ldots D_7$. The collimator laminations are made of a radiation-absorbing material, for example, sheets of a copper/silver alloy having a thickness of 0.2 mm.

Because the collimators intersect one another at the point 7, all detector elements "see" only this point, a portion of the beam 3 or the area of the primary beam 3 around this point. The scatter angles of the scattered radiation detected by the detector elements $D_1 \ldots D_7$ increase from the inside ($D_1$) to the outside ($D_7$).

It is to be noted that for the sake of clarity the drawing does not show the true geometrical relationships. The height of the collimators amounts to 300 mm whilst the diameter of the outer collimator (at its side facing the detector) amounts to 70 mm. The point 7 is situated at a distance of 500 mm from the detector arrangement D.

For these dimensions, only scattered radiation which encloses an angle (the scatter angle) of between 2 and 4 degrees with respect to the primary beam is incident on the detector elements $D_1 \ldots D_7$. In this angular range the elastic or coherent scattered radiation dominates the Compton scattered radiation in the case of a tube voltage of, for example 160 kV. The elastic scattered radiation is caused by scattering processes in which the energy of the X-ray quanta does not change.

As is known, the pulse transfer spectrum of elastically scattered radiation depends essentially on the atomic composition of the body in which the scattered radiation is produced. For example, the pulse transfer spectrum of bones exhibits a maximum at 1.8/nm, whilst the maximum of fat is situated at 1.2/nm. Therefore, it suffices to limit the determination of the pulse transfer spectrum to a range of between $X=0.8/\text{nm}$ and $X=2.0/\text{nm}$. When the outer detector element $D_7$ is to contribute to the determination of the lowest pulse transfer ($X=0.8/\text{nm}$) and the inner detector element $D_1$ is to contribute to the highest pulse transfer ($X=2/\text{nm}$), the energy of the X-ray quanta in the primary beam 3 should be between approximately 30 keV and 130 keV. This implies that the X-ray tube should operate at a voltage in excess of 130 kV, for example 160 kV.

FIG. 2 shows diagrammatically the block diagram of an arrangement for determining the pulse transfer from the output signals of the detector. In this Figure the central detector element $D_0$ and each of the ring-shaped detector elements $D_1, D_2 \ldots D_7$ is succeeded by an amplifier 10, 11, 12 ... 17, respectively, which amplify the output signal of the associated detector element. Preferably, the gain factors of all amplifiers are the same. The amplitude of the output signal of the detector elements is proportional to the energy of the X-ray quantum having produced the relevant output signal. Thus, the amplitude of the output signals of the amplifiers 10 ... 17 is also proportional to the energy of the X-ray quanta.

The analog output signals of the amplifiers 10, 11, 12 ... 17 are converted into digital output signals by means of analog-to-digital converters 20, 21, 22 ... 27, respectively, so that for each X-ray quantum the digital value supplied by the digital-to-analog converter corresponds to the amplitude of the detector output signal. To this end, the digital-to-analog converters may comprise, for example a respective capacitor which is charged, Wa a peak value rectifier, by the pulse-shaped output signal of the preceding amplifier and which is subsequently fully discharged again by a constant current. The discharging period is then proportional to the energy of the X-ray quantum. It can be measured by means of an electronic counting register which counts the pulses of a constant-frequency oscillator during the discharging period, the beginning of the capacitor discharging being synchronized with the oscillator pulses. The trigger signals for the digital-to-analog converters 20, 21 ... 27 are then derived from the output signals of the preceding detectors.

In conjunction with the subsequent circuits 30, 31, 32 ... 37, respectively, the analog-to-digital converters 20, 21, 22 ... 27 constitute pulse height analyzers which measure the frequency distribution of the amplitudes of the detector output signals. Because the amplitudes of the detector output signals are proportional to the energy of the X-ray quanta, the pulse height analyzers thus each supply the energy spectrum of the X-rays incident on the individual detector elements $D_0, D, \ldots D_7$.

To this end, the circuits $30 \ldots 37$ may comprise a respective memory and an adder. Each time when one of the analog-to-digital converters $20 \ldots 27$ has converted a voltage pulse into a digital data word, the address corresponding to the relevant data word in the memory is addressed and the associated adder is activated. The adder adds a 1, to the contents of the addressed memory location and writes the result back in the relevant memory location again, so that its contents are increased by 1. At the end of an X-ray examination, the memory locations of each memory contain the number of X-ray quanta in the energy range associated with the relevant memory location, so that the energy spectrum is thus separately stored for each detector element.

The graduation of the energy ranges in which the number of incident X-ray quanta is determined should be so fine that the accuracy of determination of the spectrum depends only on the energy-sensitivity of the detector elements. For example, when the detector elements are capable of reliably distinguishing energy differences of 300 eV, the width of the individual energy ranges in which detection takes place should be smaller than 300 eV. When the lowest energy to be detected is 30 keV and the highest energy to be detected is 130 keV, this mean s that, for example (or 1000) energy ranges should be present and that each pulse height analyzer should comprise a corresponding number of memory locations.

Figure 3A:
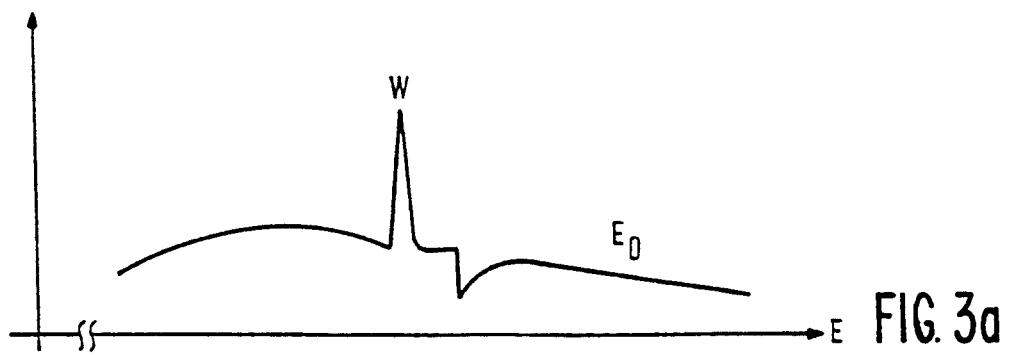
FIGS. 3a–3d shows the energy spectra of different detector elements and the pulse transfer spectrum resulting therefrom.
Figure 3B:
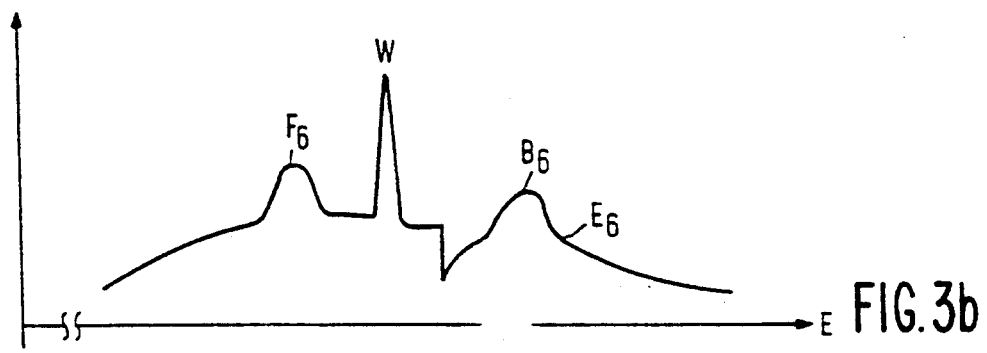
Figure 3C:
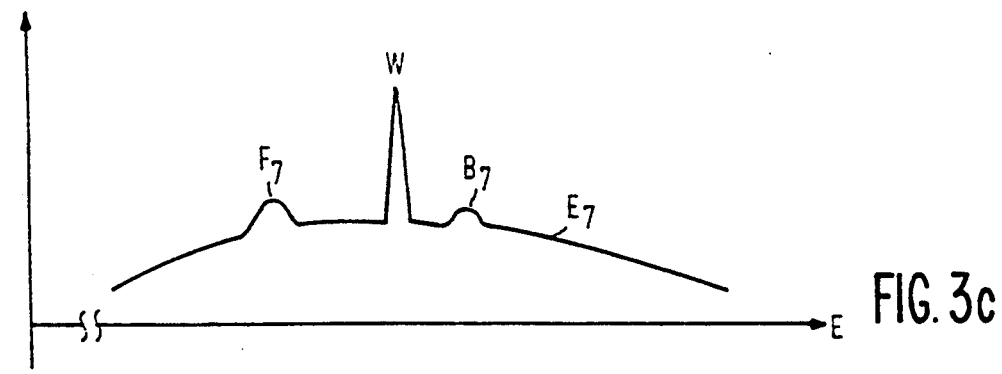

FIGS. 3a, 3b, 3c show the energy spectra, i.e. the number of X-ray quanta as a function of their energy, for different detector elements.

FIG. 3a shows the energy spectrum $E_0$ detected by the central detector element $D_0$. It is determined by the emission spectrum of the X-ray source and by the energy-dependency of the attenuation of the X-rays by the object 4 (low-energy X-ray quanta are attenuated more than high-energy quanta). A distinct line W which is produced by the characteristic radiation of the X-ray source can be recognized as well as a (relative) minimum which is caused by the absorption edge of the X-ray source. When the X-ray source comprises a tungsten anode, the characteristic line W is situated at approximately 59 keV and the absorption edge is situated at approximately 69 keV.

FIG. 3b shows the energy spectrum $E_6$ of the X-ray quanta incident on the detector element $D_6$. On the one hand, similar structures occur as in the energy spectrum $E_0$ (FIG. 3a), and on the other hand in this spectrum additionally contains two (relative) maxima $F_6$ and $B_6$ which are comparatively flat. The maximum $B_6$ (at approximately 47 keV) is caused by the fat components in the point 7 (FIG. 1), whilst the maximum $B_6$ (at approximately 72 keV) is due to the bone component.

FIG. 3c shows the energy spectrum $E_7$ of the detector element $D_7$ which has a radius greater than that of the detector element $D_6$ and which thus receives the scattered radiation from the point 7 at a greater scatter angle. Again two maxima $F_7$ and $B_7$ can be distinguished, but these maxima have been shifted towards lower energies in comparison with the spectrum $E_6$.

In order to enable determination of a common pulse transfer spectrum from the energy spectra detected by the individual detector elements, first the energy-dependency of the radiation emitted by the X-ray source and the attenuation of the radiation by the object 4 to be examined must be corrected. To this end, use is made of the fact that, because of the comparatively small scatter angles (2°–4°), the scattered radiation reaching the detector elements $D_1 \ldots D_7$ is attenuated by the object 4 to be examined to substantially the same as the primary beam 3 whose intensity behind the object to be examined is detected by the central detector element $D_0$. The energy-dependency of the radiation emitted by the X-ray source 1 also becomes manifest in the primary beam in the same way as in the scattered radiation. Therefore, when the spectra $E_1 \ldots E_7$ are each normalized to the spectrum $E_0$ by dividing, for each energy range, the number of X-ray quanta detected by the relevant detector element by the number of X-ray quanta detected by the detector element $D_0$ in the same energy range, the described energy-dependency is eliminated and also any variations of the radiation dose detected behind the object during an examination.

The described correction is performed by units 41, 42 $\ldots$ 47 which succeed the pulse height analyzers formed by respective A/D converters and circuits 21, 31 $\ldots$ 27, 37 and in which each number stored in a memory location of a pulse height analyzer memory and adder circuit associated with the detector elements $D_1 \ldots D_7$ is divided by the number stored at the relevant memory location in the circuit 30.

In addition to the described correction, the correction units 41 $\ldots$ 47 can perform further corrections, for example background radiation correction. This background radiation is caused essentially by the collimators. It can be determined once by determining the energy spectrum of the scattered radiation when a model object is arranged in the primary beam 3, which model object does not cover the point 7 and its direct vicinity. It is stored and can be subtracted during subsequent measurements, preferably prior to the normalization to the spectrum of the central detector.

The corrected spectra $E_1, \ldots E_7$, thus determined are stored in a respective memory 51, 52 $\ldots$ 57. They correspond to the spectrum which would be obtained if the X-ray source were to emit a "white" spectrum (with a constant energy-independent intensity) and if only the point 7 of the object 4 to be examined were present in the beam path, but not the whole remainder of the object to be examined and also not the collimator arrangement 6.

The following relation exists between the pulse transfer X according to the equation (1) and the energy E of an X-ray quantum scattered at the scatter angle T:

$$X = c^* E^* \sin(T/2) \tag{2}$$

where c is a constant term. When the energy E is expressed in keV and the pulse transfer X is expressed in 1/nm, c has the value 0.8066. From this equation and from the FIGS. 3b and 3c it appears that the energy associated with a given pulse transfer is higher as the scatter angle is smaller, i.e. as the detector element is situated further inwards. The energies associated with the same pulse transfer, for example $F_6$ and $F_7$ in the FIGS. 3b, and 3c, are substantially inversely proportional to the scatter angle at which the relevant detector elements are struck by scattered radiation.

The calculations according to the equation (2) are executed by a computer 18, for example a microcomputer. For each scatter spectrum E', in accordance with the associated scatter angle T these calculations produce a pulse transfer scale X which deviates as regards the sample points. The scatter spectra are added, therefore, only after conversion to uniform sample points in the X-scale by interpolation. The addition of the spectra is weighted by weighting values previously determined once in an empiric fashion. It is generally necessary in order to take into account the different quality of the individual spectra. The pulse spectrum thus determined is stored in a register 19 and is thus available for further evaluation. It can be displayed on a suitable display unit 28.

Figure 3D:
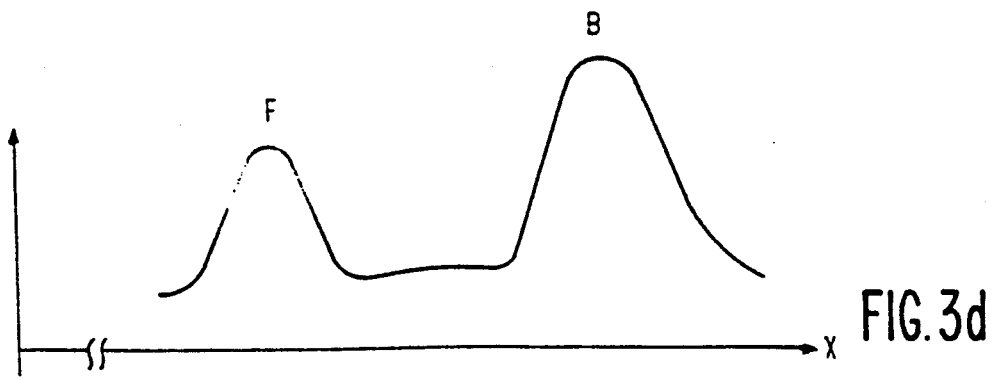

FIG. 3d shows an example of such a pulse transfer spectrum. Such a pulse transfer spectrum can occur when the point of examination 7 is situated in the spongoid bone tissue, notably the vertebral column. This pulse transfer spectrum exhibits a maximum F (at approximately 1.2/nm) which originates from the fat component in the point 7, and a maximum B which originates from the bone component and which is situated at approximately 1.8/nm. The quotient of B and F, or of the area below B and F, is a suitable measure of the mineral contents or the rigidity of a bone. The higher this quotient, the better the condition of the bone tissue.

In addition to the calculation of the pulse transfer, the microcomputer 18 can also execute other functions, for example the correction of the energy spectra. In that case the correction units 41 . . . 47 would be replaced by appropriate programming of the microcomputer.

When the scattered radiation of the structure in the point of examination does not have a preferred orientation, a rotationally symmetrical diffraction pattern is obtained. However, if this is not the case, it may be interesting to measure the elastic scattered radiation as a function of the azimuthal component. In that case each of the detector rings $D_1 \ldots D_7$ should be subdivided into a plurality of, for example eight arc-like segments for which a larger number of processing channels should be provided (for example, 11 . . . 51). FIG. 1b shows an appropriately subdivided detector ring. However, because diametrically oppositely situated segments usually are exposed to the same scatter intensity, these circuits would only be required for each time two segments.

Instead of the subdivision of the detector rings, the detector D could be preceded by a diaphragm which leaves each time only two oppositely situated sectors of the rings exposed, so that scattered radiation can be measured only in the relevant sectors. Subsequently, the diaphragm could be rotated so that other sectors would be struck by scattered radiation. The dose applied to the object 4 to be examined is then increased; however, the number of processing channels would be smaller than in the case of detector elements subdivided according to FIG. 1b.

The invention has been described in conjunction with a medical-diagnostic application. However, it can in principle be used also for other applications, for example for the testing of materials.

We claim:

1. An X-ray apparatus, comprising a polychromatic X-ray source for generating a primary beam of limited cross-section along a primary beam path, an energy-sensitive detector means comprising a central detector element situated in the primary beam path and a sequence of detector elements arranged on rings of successively increasing diameter surrounding said primary beam for detecting scattered radiation generated by elastic scattering processes in the primary beam path, a collimator means between the X-ray source and the sequence of detector elements and which encloses the primary beam, said collimator means being constructed in a manner that scattered radiation from said elastic scattering processes occurring within a given portion of the primary beam path is incident on a plurality of said sequence of detector elements, and further comprising means for determining a pulse transfer spectrum from energy spectra of X-ray quanta incident on the respective detector elements of said sequence which are normalized to an energy spectrum of X-ray quanta incident on the central detector element.

2. An X-ray apparatus as claimed in claim 1, further comprising means for normalizing the energy spectra of X-ray quanta incident on the respective detector elements of said sequence to the energy spectrum of said X-ray quanta incident on the central detector element.

3. An X-ray apparatus as claimed in claim 2 wherein the collimator means comprises a plurality of collimator laminations which are concentric with the primary beam and which are shaped as a truncated cone surface, having prolongations intersecting one another substantially in a same point located in said given portion of the primary beam path.

4. An X-ray apparatus as claimed in claim 1 wherein the collimator means comprises a plurality of collimator laminations which are concentric with the primary beam and which are shaped as a truncated cone surface, having prolongations intersecting one another substantially in a same point located in said given portion of the primary beam path.

* * * * *